United States Patent [19]

Baba et al.

[11] Patent Number: 4,651,005

[45] Date of Patent: Mar. 17, 1987

[54] ENERGY SEPARATED QUANTUM-COUNTING RADIOGRAPHY

[75] Inventors: Sueki Baba, Suita; Osamu Yamamoto, Moriguchi; Tadaoki Yamashita, Hirakata; Hiroshi Tsutsui, Yawata, all of Japan

[73] Assignee: Matsushita Electric Industrial Co., Ltd., Kadoma, Japan

[21] Appl. No.: 658,995

[22] Filed: Oct. 9, 1984

[30] Foreign Application Priority Data

Oct. 12, 1983 [JP] Japan .................. 58-189197

[51] Int. Cl.⁴ ........................................ G01N 23/08
[52] U.S. Cl. .............................. 250/360.1; 250/370; 378/5; 378/16
[58] Field of Search ....... 250/360.1, 370 JX, 370 GX, 250/370 G, 370 E; 378/5, 16, 19, 62, 63, 82

[56] References Cited

U.S. PATENT DOCUMENTS

| | | | |
|---|---|---|---|
| 3,965,358 | 6/1976 | Macovski | 378/5 |
| 4,149,081 | 4/1979 | Seppi | 378/5 |
| 4,255,659 | 3/1981 | Kaufman et al. | 250/370 |

FOREIGN PATENT DOCUMENTS

| | | | |
|---|---|---|---|
| 2636562 | 2/1978 | Fed. Rep. of Germany | 378/5 |
| 59-94046 | 5/1984 | Japan | |
| 59-100885 | 6/1984 | Japan | |

Primary Examiner—Janice A. Howell
Assistant Examiner—Constantine Hannaher
Attorney, Agent, or Firm—Cushman, Darby & Cushman

[57] ABSTRACT

In energy separated quantum-counting radiography according to the present invention, radiation penetrating the subject being examined is detected as pulses. The pulses are counted for each radiation energy group, each comprising a separate pulse height group, to thereby speedily obtain a high resolution radiation image of the various materials of the subject.

7 Claims, 9 Drawing Figures

ENERGY SEPARATED QUANTUM-COUNTING RADIOGRAPHY

BACKGROUND OF THE INVENTION

1. Field of the Invention

The present invention relates generally to an energy separated quantum-counting radiography employed for diagnosis, industrial applications and the like.

2. Description of the Prior Art

Quantum-counting radiography is known for obtaining a two dimensional image by scanning an array of radiation sensitive semiconductor elements to detect pulses representative of the amount of radiation which has penetrated a human body, the number of pulses detected producing image intensity. Such quantum-counting radiography can achieve a highly sesitive and high resolution radiation image (as disclosed in the Japanese applications of No. Sho 57-204053 and No. Sho 57-210761). However, since the above-known quantum-counting radiography devices detect the number of rays regardless of the quantity of their energy, radiation having different energies is counted as the same radiation. Therefore, conventional quantum-counting radiography has the disadvantage that complicated operation is necessary for obtaining a radiation image having as to the composition or density of the object or body being examined.

SUMMARY OF THE INVENTION

The purpose of the present invention is to provide improved quantum-counting radiography which can detect in real-time the composition or density distribution of the subject examined on the basis of information mainly involving the amounts of the radiation having penetrated the subject, the amounts being discriminated by radiation ray energy groups, thereby overcoming the disadvantages of conventional quantum-counting radiography.

The quantum-counting radiography process of the present invention comprises the steps of:

emitting rays from a radiation source, receiving by means of a linear or arc-shaped array of radiation sensitive elements the rays which have penetrated the subject being examined and changing continuously or intermittently the relative spatial relationship between the radiation source or the radiation sensitive elements and the subject, thereby producing signals containing radiographic information, characterized by the radiation sensitive elements comprising semiconductor elements. For simultaneously receiving the rays to detect the radiation as pulses, emitting radiation having different energies or a wide energy band, amplifying pulses produced by the semiconductor elements, discriminating heights of the amplified pulses, thereby classifying the pulses into groups by ranges of pulse height, counting for a predetermined time the number of pulses belonging to respective groups, and obtaining radiation image information by utilizing the number of pulses belonging to each group.

The energy separated quantum-counting radiographic apparatus according to the present invention comprises:

a source for emitting radiation rays, a linear or arc-shaped array of radiation sensitive elements for receiving radiation rays which have penetrated the subject being examined, means for altering the radiation source or the radiation sensitive elements relative to the subject whereby a radiation image of the object body is obtained, characterized in that the radiation sensitive elements comprise semiconductor elements for receiving the rays to detect the radiation as pulses, the apparatus further comprising a pulse amplifier connected to each radiation sensitive element, a pulse discriminator for discriminating pulse heights of the amplified pulses, thereby classifying the pulses into groups by ranges of pulse height, a counter for counting for a predetermined time the number of pulses belonging to each group, and a computer for receiving the number of each group counted by the pulse counter and for producing a radiation image of the subject.

DESCRIPTION OF PREFERRED EMBODIMENT

Figure 1A:
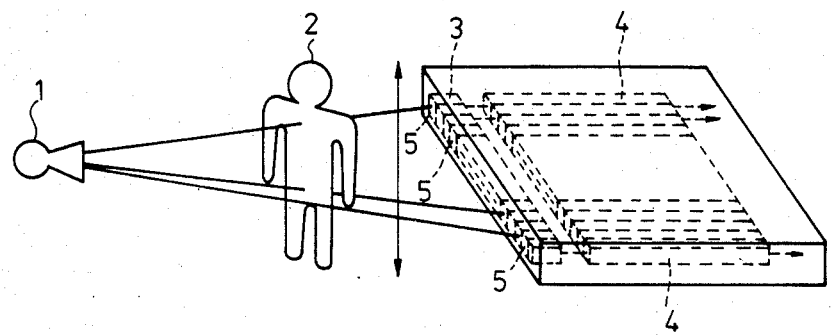
FIG. 1(a) is a perspective view diagrammatically illustrating the energy separated quantum-counting radiography arrangement of the present invention.

FIG. 1(a) is a perspective view of one embodiment of the invention illustrating the principle of energy separated quantum-counting radiography.

A subject 2, such as a human body, is disposed between a radiation source 1, for example, an X-ray source and an array 3 of radiation sensitive elements 5, 5, . . . . A circuit 4 for processing signals issued from the radiation sensitive elements 5, 5, . . . of the array 3, is connected to each radiation sensitive element 5, 5, . . . of the array 3.

Radiation having different amounts of energy or a wide energy band are emitted from slits of the radiation source 1 towards the array 3 of the radiation sensitive elements 5, 5, . . . . The radiation penetrates the body 2. The linear or arc-shaped array 3 of the radiation sensitive elements 5, 5, . . . receives the rays which have penetrated through the body, and counts the amount of the radiation received as pulse numbers. The radiation source 1 and the array 3 of the radiation sensitive elements 5, 5, . . . are displaced from an upper position to a lower position at a constant velocity, thereby producing a radiation image of the entire body 2. In place of displaying the array 3, a very large number of arrays 3, 3, . . . may be stacked together.

Figure 1B:
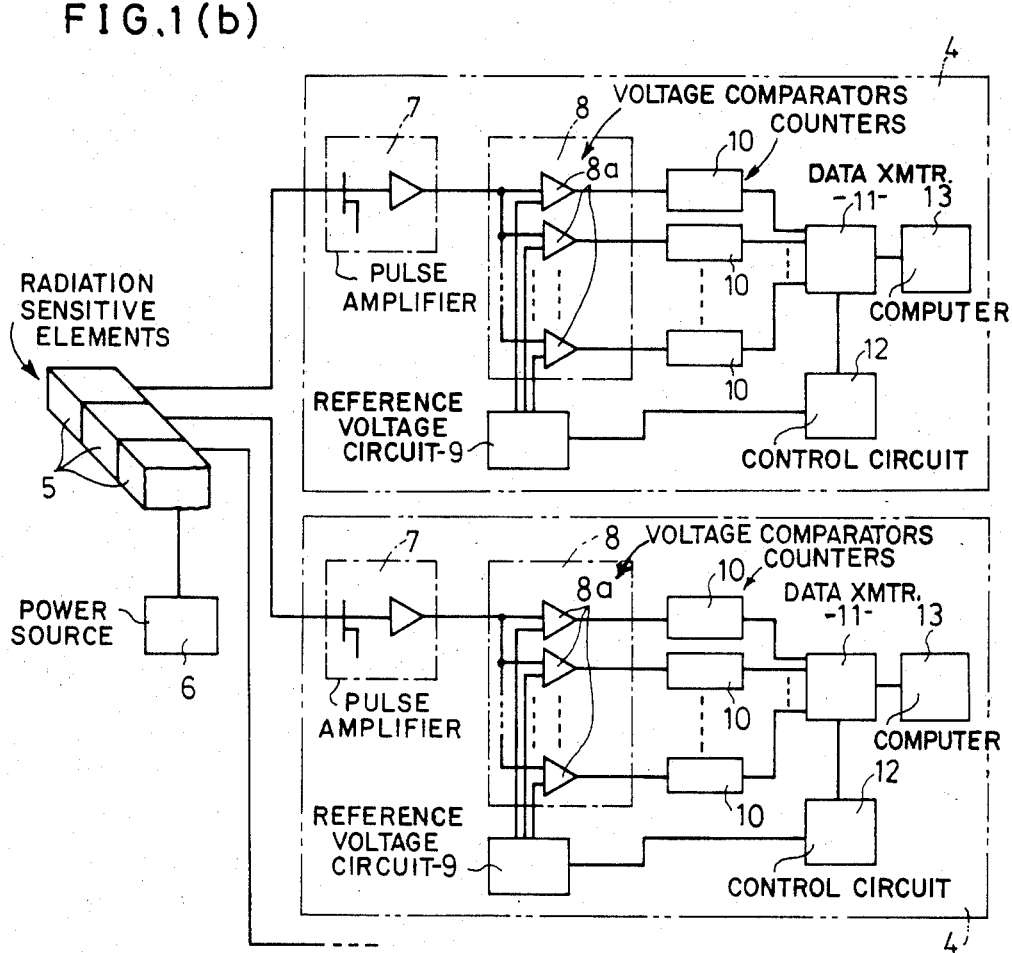
FIG. 1(b) is a circuit diagram of an array of radiation sensitive elements and other circuits of the energy separated quantum-counting radiography arrangement shown in FIG. 1(a).

FIG. 1(b) is a circuit diagram showing details of the array 3 of the radiation sensitive elements 5, 5, . . . and the circuit 4. Each of the radiation sensitive elements 5 is made of a semiconductor, such as Si, GaAs, or CdTe. An electric power source 6 supplies a voltage to the radiation sensitive element 5 for driving it. A pulse amplifier 7 is connected to each radiation sensitive element 5 and, a FET is used in the input part of the pulse amplifier 7 to form a high input impedance circuit. A pulse height discriminator 8 is connected to each pulse amplifier 7. The pulse height discriminator 8 comprises plural voltage comparators 8a, 8a, . . . to each of which the pulse issued from the pulse amplifier 7 is supplied. A reference voltage circuit 9 produces various reference voltage signals corresponding to pre-determined various pulse heights. The pulse heights are selected corresponding to respective energies of the radiation. The various reference voltage signals are supplied to each voltage comparator 8a as shown in FIG. 1(b). The voltage comparator 8a compares the pulse height corresponding to radiation energy of the pulse issued from the pulse amplifier 7 with the reference voltage signal corresponding to a predetermined height of pulse supplied to the voltage comparator 8a, thereby producing an output pulse only when the pulse height of the received pulse is larger than the reference voltage. Thus, the pulse height discriminator 8 discriminates the pulse height of the amplified pulses, thereby producing pulses grouped in accordance with classified ranges of pulse heights.

Pulse counters 10, 10, . . . for counting within a predetermined time the number of pulses issued from the respective voltage comparators 8a, 8a, . . . and memorizing the number, are connected to the voltage comparators 8a, 8a, . . . respectively. The counts of the respective pulse counters 10, 10, . . . are transmitted by a data transmitter 11 to a computer 13. A control circuit 12 controls the data transmitter 11 and the reference voltage producing circuit 9.

The operation and effect of the above-described embodiment is as follows.

The amount of radiation which has penetrated through the body is detected as a number of pulses since the quantum of the radiation gets into a depletion layer of the semiconductor element 5. As a result, a highly sensitive and high resolution radiation image can be produced at a high speed. Furthermore, an analysis of the composition and density of the various materials of the body 2 also can be executed at the same time, as described below.

The principle of the analysis is that the body 2 is disposed in a uniform radiation field, and the radiation image is obtained by detecting unevenness of the penetrating radiation, the unevenness being produced by the shielding of the body 2. The shielding is caused by radiation absorption in the materials of the body 2. The absorption amount is determined by the the amount of the energy of the radiation, its wave band, and kind and amount of the material of the body. Therefore, the kind and amount of the body materials can be analyzed by simultaneously irradiating with rays having various energy levels and detecting the absorption amount, namely, pulse numbrs corresponding to the amount of penetrating radiation for level of energy of radiation, i.e., for each pulse height. As a result, an image of high sensitivity and resolution is speedily obtained. In this embodiment, the absorption amount is obtained based on the number of pulses issued from the radiation sensitive element 5.

Figure 2:
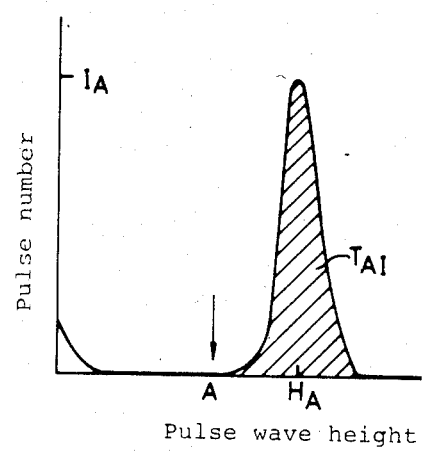
FIG. 2(a) is a graph showing a pulse height spectrum distribution with respect to a substantially uniform energy X-ray which has not penetrated through a subject being examined.
FIG. 2(b) is a graph showing a pulse height spectrum distribution with respect to the substantially uniform energy X-ray after it has penetrated through the subject.
Figure 2:
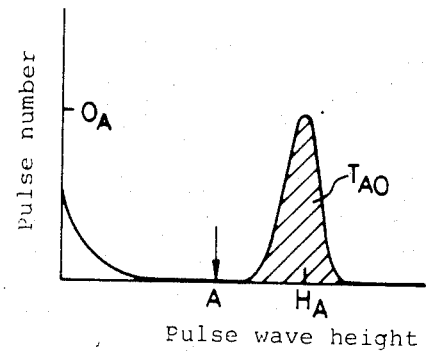

FIG. 2(a) shows the pulse height spectrum distribution, obtained from the pulse amplifier 7, of an X-ray having uniform energy which has not penetrated the body.

FIG. 2(b) shows the pulse height spectrum distribution, obtained from the pulse amplifier 7, of an X-ray having uniform energy which has not penetrated the body.

The pulse height spectrum distribution shown in FIG. 2(a) has a narrow width with a pulse height $H_A$ at its central position and a peak value $I_A$ for the number of pulses.

The pulse height spectrum distribution shown in FIG. 2(b) has a narrow width with a pulse height $H_A$ at its central position, as in FIG. 2(a), but with a peak value $O_A$ for the number of pulses a value lower than the peak value $I_A$ in FIG. 2(a).

The correlation of the peak value $O_A$ and the peak value $I_A$ is shown by the following formula (1):

$$O_A = I_A \{1 - e^{-(\Sigma \mu_n x_n)}\} \quad (1),$$

wherein $\mu_n$ is the linear absorption coefficient of the material of the body [cm$^{-1}$] and $x_n$ is virtual thickness [cm] of the body having $\mu_n$.

In this embodiment, in place of the peak value $I_A$, an integrated value $T_{AI}$, as shown by hatched lines in FIG. 2(a), is used, this value being obtained by integrating the total number of pulses having larger pulse height than the smallest pulse height A in order to avoid noise such as drift of the circuit. Likewise, in place of the peak value $O_A$, an integrated value $T_{AO}$ as shown by hatched lines in FIG. 2(b), is used, this value being obtained by integrating total number of pulses having larger height than the smallest pulse height A. The integrating operation is executed in the counter 10.

The correlation between the integrated value $T_{AI}$ and the integrated value $T_{AO}$ is shown by the next formula (2):

$$T_{AO} = T_{AI} \{1 - e^{-(\rho \mu_n x_n)}\} \quad (2).$$

Pulses having smaller pulse height than the pulse A include various noises, and these pulses can be avoided by the pulse height discriminator 8. Therefore deterioration of the radiation image caused by noise can be prevented in the present invention.

Figure 3A:
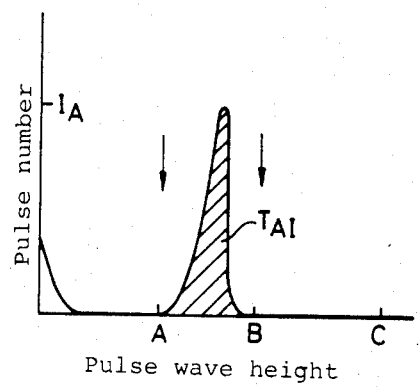
FIG. 3(a) is a graph showing another pulse height spectrum distribution with respect to a uniform energy X-ray before its penetration through the subject.
Figure 3B:
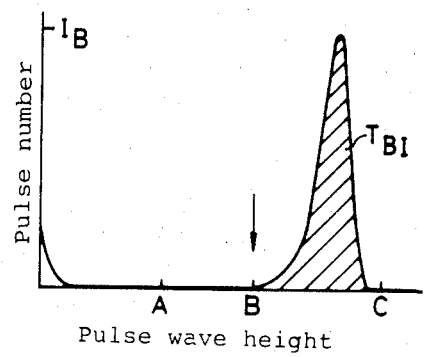
FIG. 3(b) is a graph showing a pulse height spectrum distribution with respect to still another uniform energy X-ray which has not penetrated through the subject.
Figure 3C:
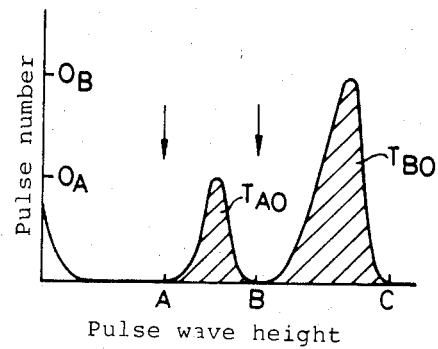
FIG. 3(c) is a graph showing a pulse height spectrum distribution with respect to X-rays having two energies shown in FIGS. 3(a) and 3(b), after they have penetrated through the subject.

FIG. 3(c) shows pulse height spectrum distribution, obtained from the pulse amplifier 7, of two X-rays which have penetrated the body and which have different energy levels, as shown in FIGS. 3(a) and 3(b). These rays are emitted simultaneously from the radiation source 1. The energy of the X-ray corresponds to the height of the pulse.

The pulse signal issued from the pulse amplifier 7 is supplied to each one of the plural voltage comparators 8a of the pulse height discriminator 8. Each voltage comparator 8a compares the pulse height of the pulse signal with a reference signal and issues output pulses only when the pulse height is larger than the reference voltage. The pulse height discriminator 8 discriminates simultaneously the pulse signals having various pulse heights, as shown in FIG. 3(c), into groups each having a certain pulse height range, for example, a group of height A to B and another group of height B to C. Therefore, various information with regard to the X-ray can be obtained by one irradiation.

FIGS. 3(a), (b) and (c) relate to X-rays at two energy levels, but the energies of the X-rays are not limited to two. The number can be increased so long as it is possible to separate the heights from each other.

The various pulse signals are supplied to respective pulse counters 10 from the voltage comparators 8a, 8a, ... and the pulse counters 10, 10, ... count the numbers of pulses of the respective groups. The numbers are memorized and are transmitted to the computer 13. The differences between the number of pulses of the X-rays not having penetrated the body and the number of pulses having penetrated corresponds to the absorption amounts of the radiation. The absorption is classified according to the energy levels of the X-rays by the computer 13. The computer 13 identifies the kind or the amount of the body material utilizing the characteristics of mass absorption coefficient ($cm^2/g$) and the X-ray energy.

Figure 4:
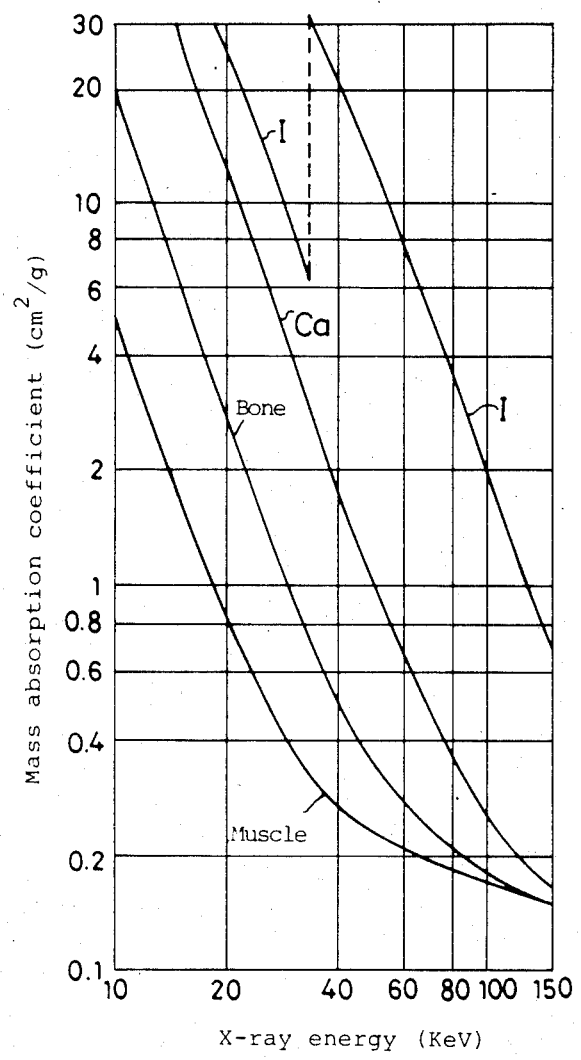
FIG. 4 is a graph showing the relationship between the mass absorption coefficient and X-ray energy with respect to the principal materials of a human body.

FIG. 4 shows the relationship between the mass absorption coefficient ($cm^2/g$) and X-ray energy (KeV) with regard to body materials. There are very large differences in mass absorption coefficients between muscle, bone, calcium (Ca) and iodine (I) which are used as contrast media in the energy region from 30 KeV to 150 KeV. For example, the mass absorption coefficient of bone is twice as large as that of muscle at 40 KeV, which is corresponds to a certain pulse height group, but the mass absorption coefficient of bone is almost as same as that of muscle at 150 KeV, which is corresponds to another pulse height group. Therefore, a radiation image of bone or a radiation image of muscle can be obtained at one time by utilizing simultaneous linear equations based on the counted number of energy group pulses and the characteristics in FIG. 4. Furthermore, a quantitative detection of bone, muscle or the like can be executed. Thus, the energy separated quantum-counting radiography of the present invention can realize a more speedy and higher resolution radiographic image than other radiation image radiographies which use a subtraction method.

Figure 5:
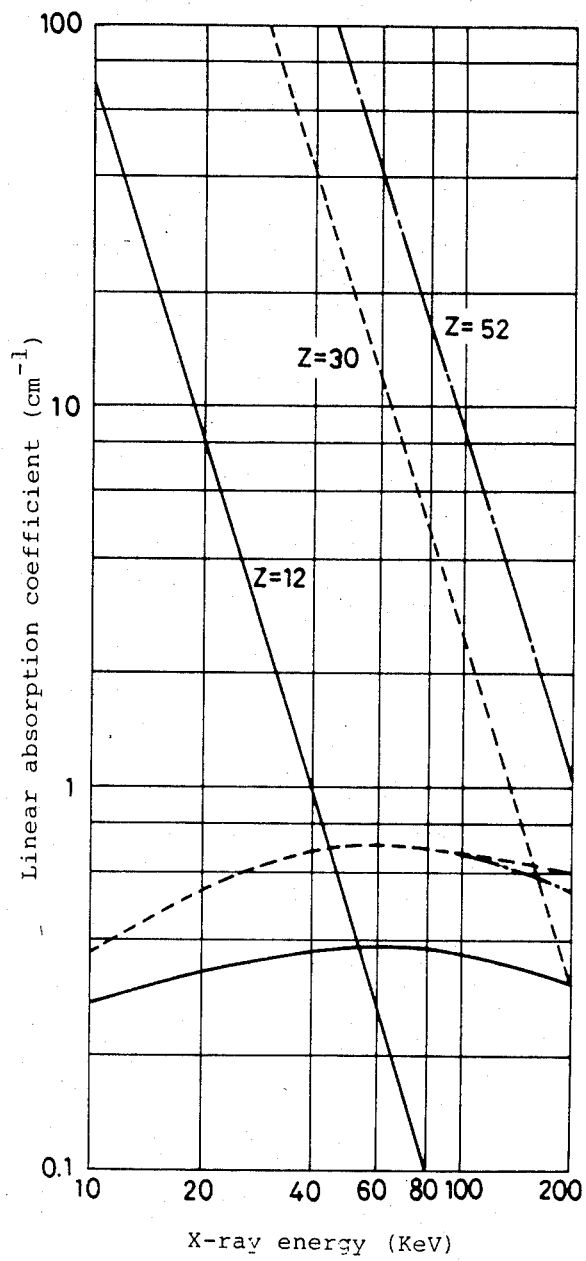
FIG. 5 is a graph showing the relationship between the linear absorption coefficient of the Compton effect and the photo-electric effect with respect to various kinds of radiation sensitive semiconductor elements.

FIG. 5 shows the relationship between the linear absorption coefficient of the Compton effect and photoelectric effect with respect to various kinds of X-ray radiation sensitive semiconductor elements. The present invention mainly uses the photo-electric effect, since a pulse output based on Compton absorption does not have a high correlation between input energy and pulse output. The Compton absorption produces noise pulses. Therefore, the present invention uses such materials as a semiconductor wherein the photo-electric absorption effect is larger than the Compton absorption effect in the energy region from that of a general medical examination to a non-destructive detecting energy region.

The source of the radiation of the present invention is a combination of an X-ray tube and a filter which can vary the energy of the X-ray, a specific X-ray beam and Radio Isotope (RI) of $^{241}$Am, Ir, etc. An electron beam which is independent of atomic number can be used together with the X-ray. Furthermore, a γ-beam, a neutron-beam or a meson-beam can used as the radiation, and these forms of radiation can be used in any combination.

The source 1 can irradiate the radiation ray continually or intermittently. Furthermore, the radiation source 1 can irradiate each energy radiation alternately or simultaneously in the case where the radiation is of different forms or has plural energy radiation levels.

As described above, energy separated quantum-counting radiography according to the present invention has the following advantages not known in the prior art.

Energy separated quantum-counting radiography of the present invention uses a pulse counting method. Therefore, a radiation image of high sensitivity and high resolution can be obtained. Furthermore, the invention counts pulses for each pulse height group. Therefore a radiation image having information as to the composition of materials of the subject being examined can be obtained speedily.

Furthermore energy separated quantum-counting radiography can be applied to computer tomography to obtain more quantitative information as to the composition of materials of the subject. The amount of the radiation directed against the subject, for example, the human body, can be decreased since energy separated quantum-counting radiography can be executed in one radiation operation.

What is claimed is:

1. An energy separated quantum-counting radiography process, comprising the steps of:

emitting radiation from a radiation source, receiving by means of a linear or arc-shaped array of radiation sensitive elements radiation which has penetrated an object being examined and continuously or intermittently altering a relative spatial relationship between either of said radiation source or said radiation sensitive elements and said object so as to induce in said element signals containing radiographic information, characterized by said radiation sensitive elements comprising semiconductor elements which simultaneously receive and detect said radiation as pulses, said elements having a photo-electric absorption effect larger than a Compton effect within a range of radiation energy levels between that used in general medical examinations and a non-destructive energy level.

said source emitting radiation having plural energy levels or a wide energy band, amplifying said pulses issued from said semiconductor elements, discriminating heights of amplified pulses so as to classify the pulses into groups by ranges of pulse height, counting for a predetermined time the number of pulses belonging to each group, and obtaining radiation image information by utilizing the number of pulses belonging to the respective groups.

2. An energy separated quantum-counting radiography process in accordance with claim 1, comprising the further steps of:
   obtaining another count of the number of pulses belonging to the respective groups with the object eliminated from a path between the radiation source and the radiation sensitive elements,
   calculating an amount of attenuation of said radiation by comparing the number of pulses belonging to the respective groups when said object, is in said path and when it is not, and
   obtaining a distribution image of either a chemical element of said object or a density of said object.

3. An energy separated quantum-counting radiography process in accordance with claim 1, wherein
   said source radiates one or plural kinds of radiation selected among an X-ray, a γ-beam, a β-beam, a neutron-beam and a meson-beam, and wherein
   each radiation has one energy level when said radiation are plural kinds.

4. An energy separated quantum-counting radiography process in accordance with claim 1, wherein
   said source irradiates one or plural kinds of radiation selected among an X-ray, a γ-beam, a β-beam, a neutron-beam and a meson-beam, and wherein
   each radiation has one energy level when said radiation are plural kinds,
   said radiation source irradiates continuously or intermittently,
   said radiation source irradiates each kind of energy radiation either alternately or simultaneously when said radiation are plural kinds of radiation or plural levels of energy radiation, respectively.

5. An energy separated quantum-counting radiographic apparatus comprising:
   a radiation source for emitting radiation,
   a linear or arc-shaped array of radiation sensitive elements for receiving radiation which has penetrated an object being examined,
   said radiation source or said radiation sensitive elements being movable relative to said object such that a radiation image of said object is obtained,
   characterized in that said radiation sensitive elements comprise semiconductor elements (to) which receive and detect said radiation as pulses, said elements having a photo-electric absorption effect larger than a Compton effect within a range of radiation energy levels between that used in general medical examinations and a non-destructive energy level,
   a pulse amplifier connected to each radiation sensitive element,
   a pulse height discriminator for discriminating heights of amplified pulses so as to classify the pulses into groups by ranges of pulse height,
   a pulse counter for counting for a predetermined time the number of pulses belonging to each group, and
   a computer for receiving the number of pulses counted by said counter, so as to obtain a radiation image of said object.

6. An energy separated quantum-counting radiographic apparatus in accordance with claim 5, wherein
   said source irradiates one or plural kinds of radiation selected among an X-ray, a γ-beam, a β-beam, a neutron-beam and a meson-beam, and wherein
   each radiation has one energy level when said radiation are plural kinds.

7. An energy separated quantum-counting radiographic apparatus in accordance with claim 5, wherein
   said source irradiates one or plural kinds of radiation selected among an X-ray, a γ-beam, a β-beam, a neutron-beam and a meson-beam, and wherein
   each radiation has one energy level when said radiation are plural kinds,
   said radiation source irradiates continuously or intermittently,
   said radiation source irradiates each kind of energy radiation either alternately or simultaneously when said radiation are plural kinds of radiation or plural levels of energy radiation, respectively.

* * * * *